United States Patent
Eichler et al.

(10) Patent No.: US 6,204,419 B1
(45) Date of Patent: Mar. 20, 2001

(54) PROCESS AND APPARATUS FOR PREPARING 1,2-DICHLOROETHANE BY DIRECT CHLORINATION

(75) Inventors: Jürgen Eichler, Kastl; Reinhard Krumböck; Wenzel Kühn, both of Burgkirchen; Peter Schwarzmaier, Kastl; Thomas Wild, Burgkirchen; Rudolf Spielmannleitner, Altötting; Manfred Stöger; Ingolf Mielke, both of Burgkirchen, all of (DE)

(73) Assignee: Vinnolit Technologie GmbH & Co. KG (DE)

( * ) Notice: Subject to any disclaimer, the term of this patent is extended or adjusted under 35 U.S.C. 154(b) by 0 days.

(21) Appl. No.: 08/480,554

(22) Filed: Jun. 7, 1995

Related U.S. Application Data

(63) Continuation of application No. 08/187,188, filed on Jan. 25, 1994, now abandoned.

(30) Foreign Application Priority Data

Jan. 27, 1993 (DE) .................................... 43 02 177
Jun. 4, 1993 (DE) .................................... 43 18 609

(51) Int. Cl.$^7$ .................................................. C07C 17/02
(52) U.S. Cl. ............................................. 570/247
(58) Field of Search ............................. 570/247

(56) References Cited

U.S. PATENT DOCUMENTS

| | | |
|---|---|---|
| 3,214,482 | 10/1965 | Caropreso et al. . |
| 3,496,243 | * 2/1970 | Berkowitz et al. ............ 570/247 |
| 3,864,411 | 2/1975 | Mueller . |
| 3,911,036 | * 10/1975 | Di Flore et al. ............... 570/247 |
| 4,672,142 | 6/1987 | Hundeck et al. . |

FOREIGN PATENT DOCUMENTS

| | | |
|---|---|---|
| 4103281 | * 8/1992 | (DE) . |
| 41 03 281 | 8/1992 | (DE) . |
| 41 33 810 | 4/1993 | (DE) . |

* cited by examiner

*Primary Examiner*—Alan Siegel
(74) *Attorney, Agent, or Firm*—Connolly Bove Lodge & Hutz LLP

(57) ABSTRACT

Process and apparatus for preparing 1,2-Dichloroethane by direct chlorination

If in the reaction of ethylene with chlorine to form 1,2-dichloroethane (EDC) the catalyst components sodium chloride and iron(III) chloride are used in a molar ratio of below 0.5, then the EDC is obtained in sufficiently high purity to allow direct conversion to vinyl chloride. With maintenance of the stated molar ratio the reaction can be carried out very advantageously in terms of equipment and energy consumption, for example by vaporizing some of the EDC in an expansion vessel.

9 Claims, 1 Drawing Sheet

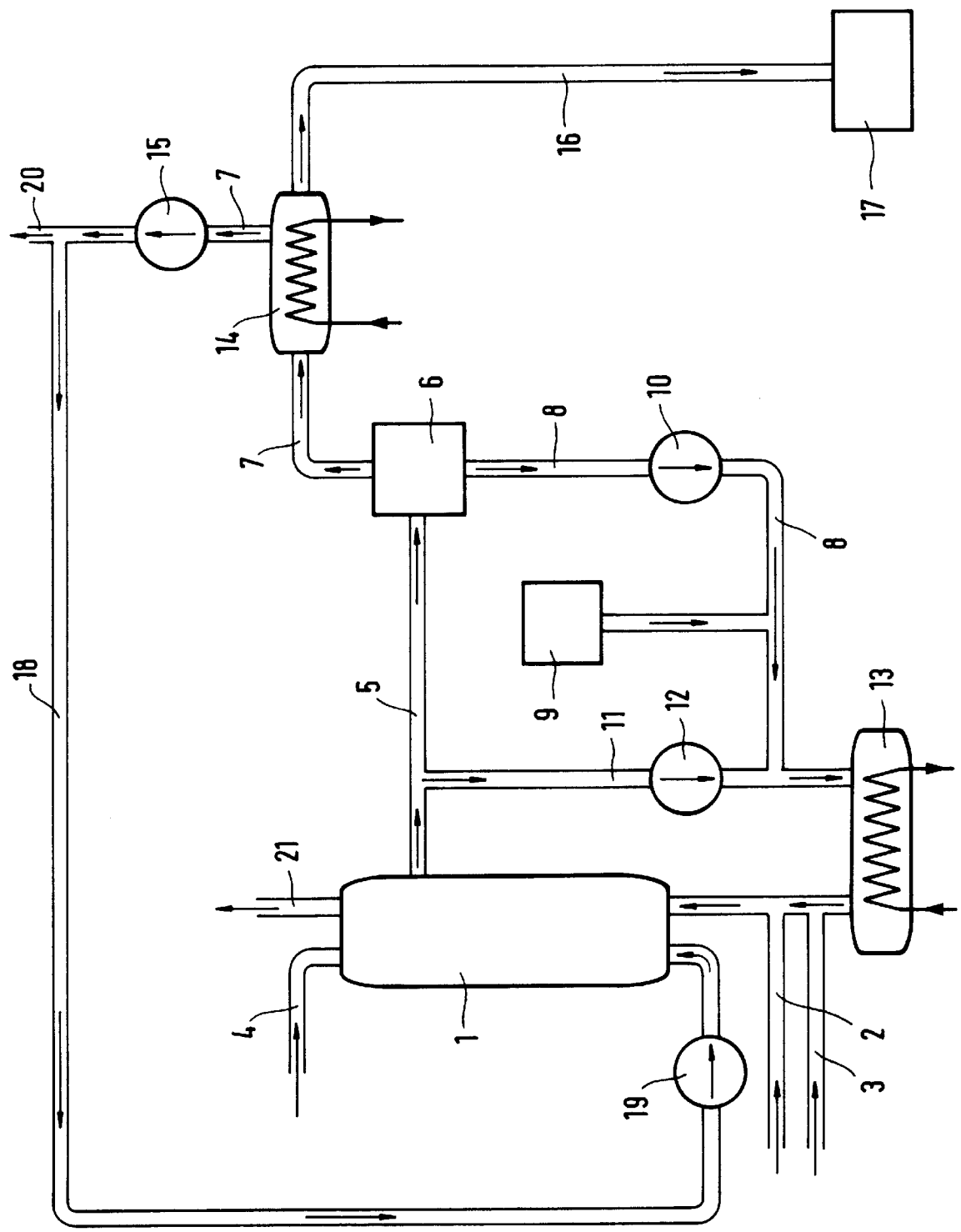

PROCESS AND APPARATUS FOR PREPARING 1,2-DICHLOROETHANE BY DIRECT CHLORINATION

This application is a continuation of Ser. No. 08/187,188 filed Jan. 25, 1994 now abandoned.

DESCRIPTION

In the so-called direct chlorination process, 1,2-dichloroethane, referred to below as EDC, is obtained by reaction of ethylene with chlorine. This addition reaction is catalyzed by metal halides which behave as Lewis acids and a halide of a metal of the first main group of the Periodic Table.

In the process described in NL-A 6901398 the metal halide having Lewis acid behavior is preferably iron(III) chloride. The metal of the first group of the Periodic Table preferably has an atomic number of at most 12 (sodium) and is in particular lithium. The molar ratio of the halide having Lewis acid behavior and the halide of the metal of the first group of the Periodic Table is between 1:2 and 2:1.

U.S. Pat. No. 4,774,373 describes a process in which the catalyst used is an anhydrous tetrachloroferrate, for example sodium tetrachloroferrate, or the corresponding components are used in stoichiometric amounts. In DE 41 03 281 Al the catalyst used is iron(III) chloride mixed with sodium chloride in a molar ratio of 1:1.5 to 1:2.

It has now been found that the direct chlorination of ethylene proceeds particularly advantageously when during the total reaction the molar ratio of sodium chloride to iron(III) chloride is kept below 0.5. Maintenance of this condition allows the reaction to be carried out in such a way as to produce EDC of sufficiently high purity to be used directly to form vinyl chloride without distillative removal of high boilers. In addition, the process of the invention is not very costly in terms of equipment and energy consumption. Preferred embodiments of the invention and the associated advantages will now be explained in more detail.

The reaction medium used is advantageously liquid EDC, the reactants being fed into the circulating EDC. Here it is not necessary to use chlorine in liquid form, since the process of the invention can be carried out under such mild conditions, particularly such low pressures, that gaseous chlorine can be used. Thus the pressure is advantageously a maximum of 1 bar gauge pressure, preferably between 0.4 and 0.6 bar gauge pressure, which is advantageously set by means of inert gas, preferably nitrogen, blanketing.

The reaction temperature is from 50 to 105° C., advantageously from 70 to 90° C. Pressure and temperature are adapted to each other in such a way that the reaction is carried out below the boiling point of EDC.

In a preferred embodiment of the invention, all or preferably only some of the EDC is passed into an expansion vessel maintained under vacuum, the heat content of the EDC stream leading to the vaporization of part of the EDC. The vaporized EDC is free of catalyst and after condensation has a purity of at least 99.9%, so that it can be fed directly to the cleavage reaction to form vinyl chloride. This allows the omission of the water-scrubbing that is necessary for removal of the catalyst in conventional processes, carried out without pressure letdown or EDC vaporization, and also of the subsequently required distillative drying of the EDC.

The pressure in the expansion vessel is advantageously from 0.2 to 0.7 bar absolute. This reduced pressure is produced and maintained by means of customary fans or pumps, referred to below as a vacuum pump. If this vacuum pump is not also to be used for conveying the gaseous EDC the latter is condensed by means of a suitable apparatus, referred to below as a cooler, and collected in a vessel.

The exploitation of the heat of reaction for the partial vaporization of the EDC and for maintaining the reaction temperature in the stated preferred range results in a substantially reduced need for coolant.

The unvaporized catalyst-containing part of the EDC remaining in the expansion vessel is returned to the EDC circuit. This is made possible by the reaction forming only a very small proportion of byproducts and the EDC return containing only inconsequential amounts of hydrogen chloride.

The waste gas is practically free of chlorine. The particularly preferred operating mode, in which only some of the EDC, preferably a relatively small amount, is passed into the expansion vessel, has the further advantage that a secondary reactor for the conversion of the remaining ethylene is not necessary. However, devices for the removal and recirculation thereof can be provided even in this preferred embodiment of the invention, since they are not very costly.

Thus the ethylene yield can be further increased or the ethylene losses further reduced by returning the ethylene-containing expansion vessel waste gas to the reaction from a point downstream of the vacuum pump by means of a suitable compressor, preferably a liquid-jet compressor, which is advantageously fitted at the bottom of the reactor, and rereacting the ethylene with chlorine. The driving jet for the preferred compressor is advantageously a bleed stream (partial stream) of the circulating EDC.

The residual amounts of ethylene can, however, also be used for producing energy by waste gas incineration, preferably for hydrogen chloride recovery.

The invention therefore also provides an apparatus which is particularly suitable for the process of the invention. It is, together with its preferred embodiments, shown in the FIGURE.

The apparatus of the invention comprises a reactor (1), feed lines (2) and (3) for ethylene and chlorine, respectively, and preferably (4) for an inert gas, a line (5) to the expansion vessel (6) which is under reduced pressure and has a line (7) for removing the vaporized product and a line (8) for returning the unvaporized product to which is preferably connected a dissolving vessel (9) and which preferably runs via a pump (10), and a line (11) for returning a product partial stream, which preferably runs via a pump (12) and a cooler or heat exchanger (13).

The line (7) for the EDC vapor advantageously runs via a cooler (14) to the vacuum pump (15). From the cooler (14) the line (16) leads to the receiver (17) for the liquefied EDC.

Advantageously, the apparatus further comprises a line (18) from the (pressure side of the) vacuum pump (15) via the compressor (19) to the reactor (1) for returning residual amounts of unreacted ethylene. (20) and (21) are lines to waste gas disposal.

If the process runs for a prolonged period it must be ensured that the sodium chloride to iron(III) chloride ratio according to the invention is maintained. So if, for example, iron(III) chloride becomes introduced into the plant, for example by corrosion, the corresponding amounts of sodium chloride must be metered in, conveniently from the dissolving vessel (9), since otherwise the purity of the distilled-off EDC deteriorates or byproduct formation increases.

The circulating EDC has an average purity of over 99%, is clear, i.e. no solid particles can be detected, and is only slightly colored. It is therefore not normally necessary to bleed off part of the stream for the purpose of removing impurities.

The examples below illustrate the invention.

EXAMPLES 1 to 4

The direct chlorination is carried out in a reactor (1) having a volume of 14.6 m$^3$ and a filling-level of 81% by volume. The pressure is maintained at 0.54 bar gauge pressure by the line (4) and the temperature is maintained at 75° C. The reaction medium is liquid EDC containing 700 ppm of iron(III) chloride.

Sodium chloride is metered into the reaction medium via a dissolving vessel (9) until the desired molar ratio of sodium chloride to iron(III) chloride (see table below) has been reached. This ratio is maintained throughout the reaction. The reactor (1) is fed with 2000 standard m$^3$/h of ethylene via line (2) and the corresponding amount of gaseous chlorine via line (3). A product bleed stream (partial stream) is conducted via line (5) into a downstream expansion vessel (6) having a pressure of 0.3 bar absolute. In this 8.90 tonnes of EDC are vaporized and drawn off via line (7). This EDC is free of catalyst and has the purity given in the table, which allows the EDC to be processed directly into vinyl chloride. The level of the byproduct 1,1,2-trichloroethane is likewise given in the table below.

The unvaporized EDC remaining in the expansion vessel (6) is returned via line (8) and a pump (10) to the reactor (1). The main product stream is fed via line (11) and a pump (12) into line (8) and returned, if necessary via a cooler (13), to the reactor (1).

In the table, Example 1 is a comparative example (without addition of NaCl), while Examples 2 to 4 are according to the invention.

TABLE

| | | Product containing | |
|---|---|---|---|
| Example | Molar ratio NaCl:FeCl$_3$ | EDC [% by weight] | 1,1,2-trichloroethane [% by weight] |
| 1 | 0 | 99.78 | 0.157 |
| 2 | 0.35:1 | 99.90 | 0.064 |
| 3 | 0.40:1 | 99.95 | 0.025 |
| 4 | 0.45:1 | 99.94 | 0.035 |

What is claimed is:

1. A process for preparing 1,2-dichloroethane by reaction of ethylene with chlorine in the presence of a sodium chloride-iron(III) chloride catalyst, which comprises maintaining the molar ratio of sodium chloride to iron(III) chloride from 0.1 to below 0.5 during the whole reaction, wherein the reaction is carried out at a pressure of up to 1 bar gauge pressure and said gauge pressure is set by inert gas blanketing.

2. The process as claimed in claim 1, wherein the molar ratio of sodium chloride to iron(III) chloride is in the range from 0.3 to 0.45.

3. The process as claimed in claim 1, wherein the reaction is carried out at from 50 to 105° C.

4. The process as claimed in claim 3, wherein the temperature is in the range from 70 to 90° C.

5. The process as claimed in claim 1, wherein the reaction is carried out at a pressure of from 0.4 to 0.6 bar gauge pressure.

6. The process as claimed in claim 1, wherein all or part of the 1,2-dichloroethane is passed to a container maintained at reduced pressure, the product which distills off being separated off and the remaining 1,2-dichloroethane being returned to the process.

7. The process as claimed in claim 1, wherein the reaction medium is circulating 1,2-dichloroethane.

8. The process as claimed in claim 1, wherein the chlorine is fed in as gas.

9. The process as claimed in claim 6, wherein said reduced pressure in said container is from 0.2 to 0.7 bar absolute.

* * * * *